United States Patent
Zhou et al.

(10) Patent No.: US 10,721,903 B2
(45) Date of Patent: Jul. 28, 2020

(54) GANODERMA LUCIDUM STRAIN SUITABLE FOR LARGE-SCALE LIQUID FERMENTATION CULTURE AND METHOD OF USING THE STRAIN

(71) Applicant: YUNNAN MINGSHIDA-SCIENCE-TECH CO., LTD., Kunming (CN)

(72) Inventors: Yingkui Zhou, Kunming (CN); Meng Zhou, Kunming (CN); Nuo Zhou, Kunming (CN)

(73) Assignee: Yunnan Mingshida-Science-Tech Co., Ltd., Kunming (CN)

( * ) Notice: Subject to any disclaimer, the term of this patent is extended or adjusted under 35 U.S.C. 154(b) by 161 days.

(21) Appl. No.: 15/923,218

(22) Filed: Mar. 16, 2018

(65) Prior Publication Data

US 2018/0199533 A1 Jul. 19, 2018

Related U.S. Application Data

(62) Division of application No. 15/057,441, filed on Mar. 1, 2016, now Pat. No. 10,028,480.

(30) Foreign Application Priority Data

Mar. 18, 2015 (CN) .......................... 2015 1 0116700

(51) Int. Cl.
| | |
|---|---|
| *C12N 1/14* | (2006.01) |
| *A01H 15/00* | (2006.01) |
| *C12N 15/01* | (2006.01) |
| *C12R 1/645* | (2006.01) |
| *A01H 1/06* | (2006.01) |
| *A01H 1/02* | (2006.01) |
| *A23L 2/38* | (2006.01) |
| *A23L 2/52* | (2006.01) |

(52) U.S. Cl.
CPC ............... *A01H 15/00* (2013.01); *A01H 1/02* (2013.01); *A01H 1/06* (2013.01); *A23L 2/382* (2013.01); *A23L 2/52* (2013.01); *C12N 1/14* (2013.01); *C12N 15/01* (2013.01); *C12R 1/645* (2013.01); *A23V 2002/00* (2013.01)

(58) Field of Classification Search
CPC ................... A01H 15/00; C12N 1/14
See application file for complete search history.

(56) References Cited

FOREIGN PATENT DOCUMENTS

| | | |
|---|---|---|
| CN | 1342752 | 4/2002 |
| CN | 1854288 | 11/2006 |
| CN | 102876581 | 1/2013 |
| CN | 103299823 | 9/2013 |
| CN | 103548556 | 2/2014 |
| CN | 204070058 | 1/2015 |
| WO | 2015018076 | 2/2015 |

OTHER PUBLICATIONS

Leskosek-Cukalovic et al Food Research International vol. 43, pp. 2262-2269 (Year: 2010).*
Ya-Jie Tang, et al., Scale-Up Study on the Fed-Batch Fermentation of Ganoderma Lucidum for the Hyperproduction of Ganoderic Acid and Ganoderma Polysaccharides, Process Biochemistry, 2011, 404-408, 46 Elsevier Ltd.
Xuan-Wei Zhou, et al., Applied Modern Biotechnology for Cultivation of Ganoderma and Development of Their Products, Applied Microbiology & Biotechnology, 2012, 941-963, 93, Springer.
Baojing Yuan, et al., Optimization of Exopolysaccharides Production from a Novel Strain of Ganoderma Lucidum CAU5501 in Submerged Culture, Brazilian Journal of Microbiology, 2012, 490-497, 1517-8382.
Yin-Ping Zhang, et al., High Preparation and Mutagenesis of Protoplast of Ganoderma Lucidum, Journal of Anhui Agri. Sci., 2012, 12379-12381, 40(25), China.
Sathesh-Prabu et al, Mutation Breeding of Mushroom by Radiation, Journal of Radiation Industry 5 (4): 285-295, 2011, 11 pages.

* cited by examiner

Primary Examiner — David H Kruse
(74) Attorney, Agent, or Firm — Sand, Sebolt & Wernow Co., LPA

(57) ABSTRACT

Disclosed is a *Ganoderma Lucidum* strain suitable for large-scale liquid fermentation, named as *Ganoderma Lucidum* G2, deposited with China General Microbiological Culture Collection Center under the accession number CGMCC No. 3982 on Jul. 20, 2010, and a method of mutation breeding the same and use of the strain. The *Ganoderma Lucidum* strain which belongs to Ganodermataceae, genus *Ganoderma*, species red *Ganoderma Lucidum* is obtained by artificial mutagenizing and breeding. The production of mycelia using the *Ganoderma Lucidum* strain G2 is 80~120 times higher as compared with the production of mycelia using wild-type naïve *Ganoderma Lucidum* strain. The mycelia produced using the *Ganoderma Lucidum* strain G2 have higher contents of main pharmaceutical ingredients. The *Ganoderma Lucidum* strain suitable for large-scale liquid fermentation can be used for manufacturing oral solution or beverage comprising *Ganoderma* mycelia or extracts of *Ganoderma* mycelia as main active ingredient.

16 Claims, No Drawings

GANODERMA LUCIDUM STRAIN SUITABLE FOR LARGE-SCALE LIQUID FERMENTATION CULTURE AND METHOD OF USING THE STRAIN

CROSS-REFERENCE TO RELATED APPLICATIONS

This is a divisional application of U.S. patent application Ser. No. 15/057,441, filed Mar. 1, 2016, the entire disclosure of which is incorporated herein by reference. U.S. patent application Ser. No. 15/057,441 claims priority from Chinese Application No. CN201510116700.1, filed Mar. 18, 2015.

FIELD OF THE INVENTION

The present application generally relates to the industry of edible fungus, and in particular, relates to a *Ganoderma Lucidum* strain suitable for large-scale liquid fermentation, a method of obtaining a *Ganoderma Lucidum* strain suitable for large-scale liquid fermentation by mutagenizing and breeding, and use of the strain.

BACKGROUND OF THE INVENTION

*Ganoderma* is recognized as a high-value herb in traditional Chinese medicine. As early as in the Donghan dynasty more than 2,000 year ago, *Ganoderma* is recorded in the "Sheng Nong's herbal classic" as a herb which is beneficial for improving general health, health of cardiac system, intelligence, spirit, health of bones, action ability and life span. *Ganoderma* is a supreme herb which refers to one having significant therapeutic effect with little side effect. Among tens of thousands of herbs, supreme herbs are very rare. During the last decades, study on *Ganoderma* mycelia becomes a hot topic worldwide.

*Ganoderma* mycelia contain cells in which the nutrients absorbed by *Ganoderma* accumulate. *Ganoderma* mycelia have rich *Ganoderma* polysaccharide, *Ganoderma* organic germanium, *Ganoderma* polypeptides, triterpenes, 16 species of amino acids of which seven are essential to human, proteins, steroid, mannitol, courmarin glycosides, alkaloids, organic acids (primarily fumaric acid), and trace elements comprising P, Fe, Ca, Mn, Zn, etc. *Ganoderma* mycelia have significant use in medical cares, e.g. anti-tumor therapy, improvement in liver health, immunity, sleep condition, and health of cardiovascular system, delaying ageing and treatment of neurasthenia. However, although wild *Ganoderma Lucidum* strain collected in nature can propagate, they have many defects in industrial production and cannot meet requirements of large-scale production of *Ganoderma* products.

SUMMARY OF THE INVENTION

The present application aims to address some issues in the prior art, and provides a *Ganoderma Lucidum* strain suitable for large-scale liquid fermentation, a method of obtaining a *Ganoderma Lucidum* strain suitable for large-scale liquid fermentation by mutagenizing and breeding, and use of the strain, so as to solve the problem that wild *Ganoderma Lucidum* strains cannot meet requirements of large-scale production of *Ganoderma* products.

In one aspect, the present application provides a *Ganoderma Lucidum* strain suitable for large-scale liquid fermentation, which is named as *Ganoderma Lucidum* G2, deposited with China General Microbiological Culture Collection Center under the accession number CGMCC No. 3982 on Jul. 20, 2010.

In one aspect, the present application provides a method of obtaining a *Ganoderma Lucidum* strain suitable for large-scale liquid fermentation by mutagenizing and breeding, the method comprising the steps of (1) subjecting pileus and stipe of non-lignified wild *Ganoderma* fruiting body to protoplast isolation, inoculating the isolate into a basic medium for culturing for 10~20 days, and subjecting the resultant *Ganoderma* mycelia to repeated isolation and purification, thereby obtaining wild-type naïve *Ganoderma* mycelia;

(2) inoculating the wild-type naïve *Ganoderma* mycelia from step (1) into a basic medium for culturing, then into a fermentation broth for culturing in a shaker, thereby obtaining a suspension of the wild-type naïve *Ganoderma* mycelia;

(3) subjecting the wild-type naïve *Ganoderma* mycelia from step (2) to a combinatory mutagenizing and breeding process of UV radiation, $NaN_3$ chemical mutagenesis and transient heating in sterile water at 80° C.~90° C., thereby obtaining a *Ganoderma Lucidum* strain suitable for efficient production of *Ganoderma* mycelia in large-scale liquid fermentation.

In one aspect, the present application provides use of a *Ganoderma Lucidum* strain suitable for large-scale liquid fermentation in manufacturing oral solution or beverage comprising *Ganoderma* mycelia or extracts of *Ganoderma* mycelia as main active ingredient.

In some embodiments, the oral solution or beverage may be a raw mycelia culture obtained from large-scale liquid fermentation of the *Ganoderma Lucidum* strain of the present application.

In some embodiments, the oral solution or beverage may be a *Ganoderma* oral solution or beverage with particular healthcare activity prepared by taking a raw mycelia culture obtained from large-scale liquid fermentation of the *Ganoderma Lucidum* strain of the present application as a main active ingredient with addition of adjuvants or excipients directed to the particular healthcare activity.

In some embodiments, the oral solution or beverage may contain extract of *Ganoderma* mycelia as a main active ingredient. The extract may be *Ganoderma* polysaccharide, *Ganoderma* organic germanium, *Ganoderma* terpenes. A *Ganoderma* oral solution or beverage with particular healthcare activity may be prepared by further adding adjuvants or excipients directed to the particular healthcare activity.

The *Ganoderma Lucidum* strain suitable for large-scale liquid fermentation of the present application is obtained by artificial mutagenizing and breeding, and is suitable for large-scale liquid fermentation. The *Ganoderma Lucidum* strain of the present application belongs to Ganodermataceae, genus *Ganoderma*, species *Ganoderma Lucidum* (W.curt.:Fr.)Karst.

The condition suitable for growth of mycelia comprises a temperature of 30° C.±1° C., pH of 4.5~5.5, culture duration of 10~12 days. The temperature suitable for growth of sporocarp is 25° C.~30° C., and its growth cycle is usually 1 to 3 years. Pileus is in semicircle, kidney or circle shape, and in woody texture. Pileus has a width of 5~15 cm, and a thickness of 0.8~1 cm. Pileus is reddish-brown and has paint gloss. Pileus has ring ridges, radial wrinkles, and a thin edge usually introverted. The flesh is white or light brown. The tube face is initially white, and then becomes light brown, and then brown. Tubes have a density of 3~5/mm Stalk grow by side or occasionally grow in a deflected direction. Stalk has a length of 3~15 cm, and a diameter of 1~3 cm. Stalk is purple-brown and has paint gloss. Spores are brown, and in an egg shape. Spores have sizes of 9~12 μm×4.5~7.5 μm. Sporocarp has a middle to large size and may be larger.

The production of mycelia using the *Ganoderma Lucidum* strain G2 of the present application is 80~120 times higher as compared with the production of mycelia using wild-type naïve *Ganoderma Lucidum* strain. The mycelia have contents of main pharmaceutical ingredients higher than those in wild-type naïve *Ganoderma Lucidum* strain, including (in wt/wt %) *Ganoderma* polysaccharide 16.8%. *Ganoderma* organic germanium 5.8%, terpenes with 28 or less C atoms 5.6%, small proteins (LZ-8) 16.6%, adenosine 3.6%, and mannitol 4.6%.

In practice, *Ganoderma* mycelia are obtained by a liquid fermentation with the following conditions:

the medium used for culturing the *Ganoderma Lucidum* strain G2 suitable for large-scale liquid fermentation of the present application has the following composition:

| | |
|---|---|
| $(NH_4)_2HPO_4$ | 0.8 g |
| $KH_2PO_4$ | 0.5 g |
| $MgSO_4\ 7H_2O$ | 0.05 g |
| NaCl | 1 g |
| $FeSO_4\ 7H_2O$ | 0.03 g |
| sucrose | 25 g |
| maltose | 5 g |
| peptone | 3 g |
| silkworm chrysalis meal | 2 g |
| extract of potato | 1000 ml; | wherein the extract of potato is prepared by cutting 300 g of potato into pieces, boiling the potato pieces in 1000 ml of purified water for 20 min followed by filtration;
and the fermentation condition comprises:
optimal culture temperature: 32±1° C.;
content of dissolved oxygen: 0.05 mmol/L~0.20 mmol/L;
pH: 4.5~5.5.

The large-scale culture lead to the yield of dry mycelia of about 6~8 g/1000 ml. Main pharmaceutical ingredients in mycelia include (in wt/wt %) *Ganoderma* polysaccharide 16.8%. *Ganoderma* organic germanium 5.8%, terpenes with 28 or less C atoms 5.6%, small proteins (LZ-8) 16.6%, adenosine 3.6%, and mannitol 4.6%.

The oral solution prepared using the *Ganoderma Lucidum* strain suitable for large-scale liquid fermentation of the present application is enriched in *Ganoderma* polysaccharide, *Ganoderma* organic germanium, triterpenes, and other active ingredients. The oral solution has a stable composition, and is advantageous in controlling blood pressure, reducing blood viscosity, cleansing blood, promoting cell activation, preventing arteriosclerosis, improving metabolism, enhancing immunity, improving sleep quality, improving male health, calming nerves, scavenging free radicals, treating and preventing cancers, and delaying aging.

According to the invention, pileus and stipe containing non-lignified *Ganoderma* sporocarp collected from nature are subjected to protoplast isolation to obtain *Ganoderma* mycelia which is then subjected to genetic breeding and mutagenizing to screen out a superior strain for large-scale production (*Ganoderma* mycelia as seed).

DETAILED DESCRIPTION OF EMBODIMENTS

The embodiments of the present application will be described with reference to the following examples. It should be understood that, the following examples are part, but not all, of the embodiments of the present application. Based on the following examples, a person skilled in the art would conceive of other variations without inventive effort, which are within the scope of the claims.

Example 1

A *Ganoderma Lucidum* strain suitable for large-scale liquid fermentation, which is named as *Ganoderma Lucidum* G2, deposited with China General Microbiological Culture Collection Center under the accession number CGMCC No. 3982 on Jul. 20, 2010.

The *Ganoderma Lucidum* strain suitable for large-scale liquid fermentation of the present application is obtained by artificial mutagenizing and breeding, and is suitable for large-scale liquid fermentation. The *Ganoderma Lucidum* strain of the present application belongs to Ganodermataceae, genus *Ganoderma*, species *Ganoderma Lucidum* (W.curt.:Fr.)Karst.

The condition suitable for growth of mycelia comprises a temperature of 30° C.±1° C., pH of 4.5~5.5, culture duration of 10~12 days. The temperature suitable for growth of sporocarp is 25° C.~30° C., and its growth cycle is usually 1 to 3 years. Pileus is in semicircle, kidney or circle shape, and in woody texture. Pileus has a width of 5~15 cm, and a thickness of 0.8~1 cm. Pileus is reddish-brown and has paint gloss. Pileus has ringlike ridges, radial wrinkles, and a thin edge usually introverted. The flesh is white or light brown. The tube face is initially white, then becomes light brown, and then brown. Tubes have a density of 3~5/mm. Stalk grow by side and occasionally grow in a deflected direction. Stalk has a length of 3~15 cm, and a diameter of 1~3 cm. Stalk is purple-brown and has paint gloss. Spores are brown, and in an egg shape. Spores have sizes of 9~12 μm×4.5~7.5 μm. Sporocarp has a middle to large size and may be larger.

The production of mycelia using the *Ganoderma Lucidum* strain G2 of the present application is 80~120 times higher as compared with the production of mycelia using wild-type naïve *Ganoderma Lucidum* strain. The mycelia have contents of main pharmaceutical ingredients higher than those in wild-type naïve *Ganoderma Lucidum* strain, including (in wt/wt %) *Ganoderma* polysaccharide 16.8%, *Ganoderma* organic germanium 5.8%, terpenes with 28 or less C atoms 5.6%, small proteins (LZ-8) 16.6%, adenosine 3.6%, and mannitol 4.6%.

The medium used for culturing the *Ganoderma Lucidum* strain G2 suitable for large-scale liquid fermentation of the present application has the following composition:

| | |
|---|---|
| $(NH_4)_2HPO_4$ | 0.8 g |
| $KH_2PO_4$ | 0.5 g |
| $MgSO_4\ 7H_2O$ | 0.05 g |
| NaCl | 1 g |
| $FeSO_4\ 7H_2O$ | 0.03 g |
| sucrose | 25 g |
| maltose | 5 g |
| peptone | 3 g |
| silkworm chrysalis meal | 2 g |
| extract of potato | 1000 ml; | wherein the extract of potato is prepared by cutting 300 g of potato into pieces, boiling the potato pieces in 1000 ml of purified water for 20 min followed by filtration;
and the fermentation condition includes:
optimal culture temperature: 32±1° C.;
content of dissolved oxygen: 0.05 mmol/L~0.20 mmol/L;
pH: 4.5~5.5.

The large-scale culture leads to the yield of dry mycelia of about 6~8 g/1000 ml. Main pharmaceutical ingredients in mycelia include (in wt/wt %) *Ganoderma* polysaccharide 16.8%, *Ganoderma* organic germanium 5.8%, terpenes with 28 or less C atoms 5.6%, small proteins (LZ-8) 16.6%, adenosine 3.6%, and mannitol 4.6%. The production of mycelia is 80-120 times higher as compared with the production of mycelia using wild-type naïve *Ganoderma Lucidum* strain.

Example 2

The method of obtaining a *Ganoderma Lucidum* strain suitable for large-scale liquid fermentation by mutagenizing and breeding comprises the following steps.

Step 1: Subjecting pileus and stipe of non-lignified wild *Ganoderma* fruiting body collected from *Prunus* mume Apricot to protoplast isolation, inoculating the isolate thus obtained into a basic medium for culturing at a temperature of 28° C.~30° C. for 15 days, and subjecting the resultant *Ganoderma* mycelia to repeated isolation and purification, thereby obtaining wild-type naïve *Ganoderma* mycelia;

wherein the basic medium used in protoplast isolation and purification carried out on pileus and stipe of non-lignified wild *Ganoderma* fruiting body has the following composition:

| | |
|---|---|
| $(NH_4)_2HPO_4$ | 0.3 g |
| $KH_2PO_4$ | 0.2 g |
| $MgSO_4 \cdot 7H_2O$ | 0.02 g |
| NaCl | 0.5 g |
| $FeSO_4 \cdot 7H_2O$ | 0.03 g |
| sucrose | 20 g |
| sterile water | 1000 ml. |

Step 2: Inoculating the wild-type naïve *Ganoderma* mycelia from Step 1 into a basic medium for culturing, then into a fermentation broth for culturing in a shaker, thereby obtaining a suspension of the wild-type naïve *Ganoderma* mycelia;

wherein (1) the components and their contents of the basic medium was optimized by a single factor orthogonal experiment, in order to obtain a medium suitable for the growth of wild-type naïve *Ganoderma*.

The orthogonal experiment was carried out as follows.

5000 ml of purified water was divided into 25 flasks with 200 ml for each. The flasks were numbered 1~25, and divided into five groups, i.e., Nos. 1~5, Nos. 6~10, Nos. 11~15, Nos. 16~20, and Nos. 21~25. Basic medium with different composition was added into the flasks respectively, as shown in table 1.

TABLE 1

(unit: g)

| basic medium Nos. | 1~5 | 6~10 | 11~15 | 16~20 | 21~25 |
|---|---|---|---|---|---|
| $(NH_4)_2HPO_4$ | 0.3 | 0.6 | 0.5 | 0.3 | 0.8 |
| $KH_2PO_4$ | 0.5 | 0.5 | 0.2 | 0.5 | 0.3 |
| $MgSO_4 \cdot 7H_2O$ | 0.02 | 0.05 | 0.04 | 0.04 | 0.05 |
| NaCl | 0.5 | 0.5 | 0.8 | 0.5 | 0.5 |
| $FeSO_4 \cdot 7H_2O$ | 0.03 | 0.03 | 0.03 | 0.03 | 0.03 |
| sucrose | 20 | 30 | 20 | 30 | 20 |
| peptone | 3 | 3 | 2 | 3 | 2 |

The medium was subjected to high pressure sterilization and then used for culturing the naïve *Ganoderma* mycelia for 12 days. Then, the mycelia in flasks No. 1~25 were filtered, and dried at a temperature of 105±1° C. for 24 h. Then, the dried mycelia were weighed, and the average weight of mycelia for each group was calculated and compared with each other. An optimal basic medium with following composition was established.

| | |
|---|---|
| $(NH_4)_2HPO_4$ | 0.6 g |
| $KH_2PO_4$ | 0.5 g |
| $MgSO_4\ 7H_2O$ | 0.05 g |
| NaCl | 0.5 g |
| $FeSO_4\ 7H_2O$ | 0.03 g |
| sucrose | 30 g |
| peptone | 3 g |
| sterile water | 1000 ml. |

(2) Based on the optimal basic medium established from the above single factor orthogonal experiment, a multiple factor orthogonal experiment was carried out by selecting different nitrogen sources, carbon sources, trace elements, culturing temperature and oxygen requirement as the factors. The optimal fermentation conditions finally established included the following.

The fermentation broth has the following composition:

| | |
|---|---|
| $(NH_4)_2HPO_4$ | 0.8 g |
| $KH_2PO_4$ | 0.5 g |
| $MgSO_4 \cdot 7H_2O$ | 0.05 g |
| NaCl | 1 g |
| $FeSO_4 \cdot 7H_2O$ | 0.03 g |
| sucrose | 25 g |
| maltose | 5 g |
| peptone | 3 g |
| silkworm chrysalis meal | 2 g |
| sterile water | 1000 ml; | and
the fermentation condition includes:
optimal culture temperature: 32±1° C.;
content of dissolved oxygen: 0.05 mmol/L~0.20 mmol/L;
pH: 4.5~5.5.

Step 3: subjecting the wild-type naïve *Ganoderma* mycelia from Step 2 to a combinatory mutagenizing and breeding process which combines UV radiation, $NaN_3$ chemical mutagenesis and transient heating in sterile water at 80° C. 90° C., thereby obtaining a *Ganoderma Lucidum* strain suitable for efficient production of *Ganoderma* mycelia in large-scale liquid fermentation.

In Step 3, UV radiation is performed first. In particular, three samples of suspensions containing wild-type naïve *Ganoderma* mycelia (10 wt/wt %) were prepared, and named as Sample 1, Sample 2 and Sample 3. the wild-type naïve *Ganoderma* mycelia were irradiated with a 40 W UV lamp from a distance of 20 cm, and the radiation durations were set as below.

| Sample No. | 1 | 2 | 3 |
|---|---|---|---|
| radiation duration (min) | 5 | 10 | 20 |

Next, Sample 2 which is irradiated for 10 min had a lethality rate of 93% was selected in further experiments.

After culturing Sample 2, three samples of suspensions containing mycelia (10 wt/wt %) were prepared, and named Sample 4, Sample 5 and Sample 6. The samples were subjected to chemical mutagenesis with a chemical mutagenesis agent.

NaN$_3$ is selected as the chemical mutagenesis agent. In particular, 1 g of NaN$_3$ of 1.2 equivalent was dissolved into a mixture of 5 ml of dimethylformamide (DMF) and 5 ml of dimethyl sulfoxide (DMSO), thereby obtaining the chemical mutagenesis agent. Sample 4, Sample 5 and Sample 6 were added to the chemical mutagenesis agent for chemical mutagenesis treatment. The durations of chemical mutagenesis were set as follows.

| Sample Nos. | 4 | 5 | 6 |
|---|---|---|---|
| duration of chemical mutagenesis (min) | 5 | 10 | 20 |

Finally, transient heating in sterile water was carried out. In particular, Sample 4, Sample 5 and Sample 6 were washed with sterile water three times using centrifugation, and then subjected to transient heating in sterile water at 80° C.~90° C. The durations of transient heating were set as follows.

| Sample Nos. | 4 | 5 | 6 |
|---|---|---|---|
| duration of transient heating ( sec ) | 1 | 5 | 10 |

Sample 6 was subjected to transient heating for 10 sec with a lethality rate of 96%. The survived strain was the *Ganoderma Lucidum* G2 which is suitable for liquid fermentation and can lead to high production of *Ganoderma* mycelia. The strain was deposited with China General Microbiological Culture Collection Center under the accession number CGMCC No. 3982.

Example 3

This example relates to a use of a *Ganoderma Lucidum* strain suitable for large-scale liquid fermentation in manufacturing oral solution or beverage comprising *Ganoderma* mycelia or extracts of *Ganoderma* mycelia as main active ingredient.

In Example 3, *Ganoderma* mycelia are obtained by large-scale liquid fermentation with the medium and conditions described in Example 1.

The *Ganoderma Lucidum* strain of the present application is subjected to large-scale liquid fermentation to yield *Ganoderma* mycelia. Then, the *Ganoderma* mycelia, as main active ingredient, are used to prepare *Ganoderma* oral solution. The *Ganoderma* oral solution is enriched in *Ganoderma* polysaccharide, *Ganoderma* organic germanium, triterpenes, and other active ingredients, and has a stable composition.

The oral solution or beverage may be a raw mycelia culture obtained from large-scale liquid fermentation of the *Ganoderma Lucidum* strain of the present application. The oral solution is advantageous in many aspects, e.g., immunity improvement, blood pressure control, lowering of blood viscosity, blood cleaning, cell activation promotion, arteriosclerosis prevention, metabolism improvement, sleep ameliorating, anti-allergy, male health improvement, nerves calming, and delaying aging.

The oral solution or beverage may also be a *Ganoderma* oral solution or beverage with particular healthcare activity prepared by supplementing a raw mycelia culture obtained from large-scale liquid fermentation of the *Ganoderma Lucidum* strain of the present application as the main active ingredient with adjuvants or excipients directed to the particular healthcare activity.

For example, polysaccharide extract of poria *cocos*, or polysaccharide extract of polyporus *umbellatus* may be added as medical adjuvants to prepare a *Ganoderma* oral solution especially beneficial to cancer patients. Vitamins or trace elements may be added as energy adjuvants to prepare a functional *Ganoderma* oral solution for improving physical ability.

We claim:

1. A method of culturing a *Ganoderma lucidum* strain named *Ganoderma lucidum* G2 that was deposited with China General Microbiological Culture Collection Center under the accession number CGMCC No. 3982 on Jul. 20, 2010 in a large-scale liquid fermentation process in manufacturing of an oral solution or a beverage that includes *Ganoderma* mycelia or extracts of *Ganoderma* mycelia as a main active ingredient.

2. The method of claim 1, wherein the *Ganoderma* mycelia is obtained by liquid fermentation with the following culture conditions:

the medium for culturing the *Ganoderma lucidurn* G2 has the following composition:

| | |
|---|---|
| (NH$_4$)$_2$HPO$_4$ | 0.8 g |
| KH$_2$PO$_4$ | 0.5 g |
| MgSO$_4$ 7H$_2$O | 0.05 g |
| NaCl | 1 g |
| FeSO$_4$ 7H$_2$O | 0.03 g |
| sucrose | 25 g |
| maltose | 5 g |
| peptone | 3 g |
| silkworm chrysalis meal | 2 g |
| extract of potato | 1000 ml; | wherein the extract of potato is prepared by boiling 300 g of potato pieces in 1000 ml of purified water for 20 minutes followed by filtration; and the fermentation condition comprises:
optimal culture temperature: 32±1° C.;
content of dissolved oxygen: 0.05 mmol/L-0.20 mmol/L; and
pH: 4.5-5.5.

3. A method of manufacturing an oral solution or a beverage comprising:

selecting the *Ganoderma lucidum* strain named *Ganoderma lucidum* G2, deposited with China General Microbiological Culture Collection Center under the accession number CGMCC No. 3982 on Jul. 20, 2010;

performing a large-scale fermentation process of the *Ganoderma lucidum* G2;

obtaining one or more of *Ganoderma* mycelia and extracts of *Ganoderma* mycelia through the large-scale fermentation process;

selecting one or more of the *Ganoderma* mycelia and extracts of *Ganoderma* mycelia; and incorporating the selected one or more of the *Ganoderma* mycelia and extracts of *Ganoderma* mycelia as a main active ingredient in an oral solution or a beverage.

4. The method according to claim 3, wherein the large-scale fermentation process is a liquid fermentation process.

5. The method according to claim 4, wherein the *Ganoderma* mycelia are obtained through the liquid fermentation process.

6. The method according to claim 5, wherein the liquid fermentation process includes:

using a medium for culturing the *Ganoderma lucidum* G2, wherein the medium has the following composition:

| | |
|---|---|
| (NH$_4$)$_2$HPO$_4$ | 0.8 g |
| KH$_2$PO$_4$ | 0.5 g |
| MgSO$_4$ 7H$_2$O | 0.05 g |
| NaCl | 1 g |
| FeSO$_4$ 7H$_2$O | 0.03 g |
| sucrose | 25 g |
| maltose | 5 g |
| peptone | 3 g |
| silkworm chrysalis meal | 2 g |
| extract of potato | 1000 ml. |

7. The method according to claim 6, further comprising: preparing the extract of potato by boiling 300 g of potato pieces in 1000 ml of purified water for 20 minutes, followed by filtration thereof.

8. The method according to claim 6, further comprising: performing the fermentation under a fermentation condition that includes:
an optimal culture temperature of 32±1° C.; a content of dissolved oxygen of 0.05 mmol/L-0.20 mmol/L; and a pH of 4.5 to 5.5.

9. The method according to claim 4, wherein the *Ganoderma* mycelia obtained from the large-scale liquid fermentation is a raw mycelia culture.

10. The method according to claim 9, further comprising: adding one or more adjuvants and excipients to the raw mycelia culture.

11. The method according to claim 10, further comprising: selecting the one or more adjuvants and excipients based on a healthcare activity for which the oral solution or beverage is to be ingested by a person.

12. The method according to claim 11, further comprising selecting one or more of a polysaccharide extract of poria *cocos* and a polysaccharide extract of polyporus *umbellatus* as adjuvants.

13. The method according to claim 11, further comprising utilizing one or more of the polysaccharide extract of poria *cocos* and the polysaccharide extract of polyporus *umbellatus* for treatment of cancer patients.

14. The method according to claim 11, further comprising selecting one or more of vitamins and trace elements as adjuvants.

15. The method according to claim 11, wherein the healthcare activity for which the one or more adjuvants and excipients are selected include blood viscosity, cleansing blood, promoting cell activation, preventing arteriosclerosis, improving metabolism, enhancing immunity, improving sleep quality, improving male health, calming nerves, scavenging free radicals, treating cancers, preventing cancers, and delaying aging.

16. The method according to claim 3, wherein the extract of *Ganoderma* obtained from the large-scale fermentation process is one of *Ganoderma* polysaccharide, *Ganoderma* organic germanium, and *Ganoderma* terpenes.

* * * * *